(12) United States Patent
Hourigan et al.

(10) Patent No.: US 9,006,163 B2
(45) Date of Patent: Apr. 14, 2015

(54) CLEANSING COMPOSITIONS WITH POLYURETHANE-34

(75) Inventors: Regina Hourigan, Metuchen, NJ (US); Jairajh Mattai, Piscataway, NJ (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/362,127

(22) PCT Filed: Dec. 15, 2011

(86) PCT No.: PCT/US2011/065022
§ 371 (c)(1),
(2), (4) Date: Jun. 1, 2014

(87) PCT Pub. No.: WO2013/089720
PCT Pub. Date: Jun. 20, 2013

(65) Prior Publication Data
US 2014/0342968 A1 Nov. 20, 2014

(51) Int. Cl.
*A61K 8/87* (2006.01)
*A61Q 17/00* (2006.01)
*A61Q 19/10* (2006.01)

(52) U.S. Cl.
CPC ............... *A61K 8/87* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 3,708,435 A | 1/1973 | Starkman | |
| 4,985,036 A | 1/1991 | Lommen et al. | |
| 5,972,354 A | 10/1999 | De La Poterie et al. | |
| 6,375,941 B1 | 4/2002 | Piot et al. | |
| 7,682,402 B2 | 3/2010 | Kravtchenko et al. | |
| 2003/0152533 A1 | 8/2003 | Tang | |
| 2003/0190294 A1 | 10/2003 | Leblanc et al. | |
| 2004/0197293 A1 | 10/2004 | Mougin | |
| 2006/0134239 A1 | 6/2006 | Weide et al. | |
| 2007/0025943 A1 | 2/2007 | Patel | |
| 2007/0154440 A1 | 7/2007 | Fleissman et al. | |
| 2007/0258932 A1 | 11/2007 | Bui et al. | |
| 2008/0166309 A1 | 7/2008 | McDermott et al. | |
| 2008/0260808 A1 | 10/2008 | Pinna et al. | |
| 2008/0299154 A1 | 12/2008 | Barrios et al. | |
| 2011/0015279 A1 | 1/2011 | Doerr et al. | |
| 2011/0097289 A1 | 4/2011 | Viala et al. | |
| 2012/0101060 A1* | 4/2012 | Thoerner et al. | 514/54 |

FOREIGN PATENT DOCUMENTS

| | | |
|---|---|---|
| EP | 212681 | 3/1987 |
| EP | 250125 | 12/1987 |
| EP | 274863 | 7/1988 |
| EP | 304536 | 3/1989 |
| EP | 335669 | 10/1989 |
| EP | 338819 | 10/1989 |
| EP | 351016 | 1/1990 |
| EP | 427474 | 5/1991 |
| EP | 584361 | 3/1994 |
| EP | 607434 | 4/1994 |
| EP | 617938 | 10/1994 |
| EP | 621042 | 10/1994 |
| EP | 638301 | 2/1995 |
| EP | 673657 | 9/1995 |
| EP | 676192 | 10/1995 |
| EP | 742006 | 11/1996 |
| EP | 774242 | 5/1997 |
| EP | 775483 | 5/1997 |
| EP | 815880 | 1/1998 |
| EP | 1010418 | 6/2000 |
| EP | 1854450 | 11/2007 |
| EP | 1914264 | 4/2008 |
| EP | 1935913 | 6/2008 |
| EP | 1938864 | 7/2008 |
| EP | 1952842 | 8/2008 |
| EP | 1978068 | 10/2008 |
| EP | 1982690 | 10/2008 |
| EP | 1997472 | 12/2008 |
| FR | 2832058 | 5/2003 |
| JP | 63280012 | 4/1988 |
| JP | 2004035544 | 2/2004 |
| WO | WO9817773 | 4/1998 |
| WO | WO0207685 | 1/2002 |
| WO | WO02083073 | 10/2002 |
| WO | WO03039445 | 5/2003 |
| WO | WO2009118107 | 10/2009 |

OTHER PUBLICATIONS

Bayer Material Science—Baycusan C 1000. Aqueous polyurethane dispersion. Pamphlet. (7 pages) Edition Sep. 2, 2011. Published by Coatings, Adhesives & Specialties, Bayer MaterialScience AG, Leverkusen, DE.

Bayer Material Science—Baycusan C 1001. Aqueous polyurethane dispersion. Pamphlet. (10 pages) Edition Sep. 2, 2011. Published by Coatings, Adhesives & Specialties, Bayer MaterialScience AG, Leverkusen, DE.

Bayer Material Science—Cosmetics—RR 8015—Baycusan C-100 Sun Lotion SPF 30. Pamphlet. Edition Mar. 15, 2010. (2 pages) Published by Coatings, Adhesives & Specialties, Bayer MaterialScience AG, Leverkusen, DE.

Bayer Material Science NAFTA—News. (3 pages) Retrieved from the internet. (Dec. 2, 2011).

(Continued)

*Primary Examiner* — Necholus Ogden, Jr.

(74) *Attorney, Agent, or Firm* — Michael F. Morgan

(57) ABSTRACT

A cleansing composition comprising a cleansing effective amount of surfactant and polyurethane-34. The polyurethane-34 can deposit on skin during cleansing and form a barrier that reduces bacterial attachment to skin.

10 Claims, No Drawings

(56) References Cited

OTHER PUBLICATIONS

International Search Report and the Written Opinion issued in International Application PCT/US11/65022 mailed Aug. 27, 2012. WO.
New Baycusan C product lne: five new ingredients for looking great, Internet Citation, May 21, 2009, pp. 1-3, XP002595522, Retrieved from the Internet: URL: http://www.bayermaterialsciencenafta.com/news/index.cfm?mode=detail&id=63CAE48F-E16D-41A1-58CBDFABC77D3B5.
Polyurethane(s) for Cosmetics—Film Forming Polymers (2 pages) www.bayercosmetics.com/bms/bms-cosmetics.nsf/id/01_LEV_EN_Film_Forming (Dec. 2, 2011).

* cited by examiner

CLEANSING COMPOSITIONS WITH POLYURETHANE-34

CROSS-REFERENCE TO RELATED PATENT APPLICATIONS

The present application is a U.S. national stage entry under 35 U.S.C. §371 of Patent Cooperation Treaty Patent Application No. PCT/US2011/65022, filed Dec. 15, 2011, the entirety of which is incorporated herein by reference.

FIELD OF THE INVENTION

The present invention relates to cleansing compositions with polyurethane-34.

BACKGROUND OF THE INVENTION

While cleansing compositions can remove bacteria from skin, new bacteria can attach to skin when skin contacts a surface containing bacteria. It would be desirable to have a protective layer on the skin to block bacteria from attaching to skin. It would be desirable to have the protective layer deposited on skin during skin cleansing.

BRIEF SUMMARY OF THE INVENTION

A cleansing composition comprising a cleansing effective amount of surfactant and polyurethane-34.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

Polyurethane-34 can be included in cleansing compositions, such as body washes/shower gels, liquid hand soaps, or bar soaps. When used to cleanse skin, the polyurethane-34 can deposit on skin and form a barrier. The barrier can reduce or prevent bacteria from attaching to skin.

Polyurethane-34 is the generic INCI name for a polyurethane polymer sold under the Baycusan™ C1000 tradename from Bayer. It is sold as a 40% polymer solution. Polyurethane-34 can be included in cleansing compositions in any desired amounts. In certain embodiments, the amount is 0.1 to 5% by weight of the composition. In other embodiments, the amount is 0.1 up to 4, 3, 2, 1.5, 1, 0.9, 0.8, 0.7, 0.6, or 0.5% by weight of the composition. In other embodiments, the amount is at least 0.2, at least 0.3, at least 0.4, at least 0.5 up to 5, 4, 3, 2, or 1% by weight. In certain embodiments, the amount is 0.1, 0.2, 0.3, 0.4, 0.5, 0.6, 0.7, 0.8, 0.9, 1, 1.5, or 2% by weight of the composition.

The cleansing composition includes a cleansing effective amount of one or more anionic surfactants, amphoteric surfactants, nonionic surfactants, cationic surfactants, and combinations thereof. The cleansing composition can be in the form of a body wash/shower gel, liquid hand soap, or a bar soap.

A variety of anionic surfactants can be utilized in the composition including, for example, long chain alkyl ($C_6$-$C_{22}$) materials such as alkyl sulfates, alkyl sulfonates, alkyl phosphates, alkyl ether sulfates, alkyl alpha olefin sulfonates, alkyl taurates, alkyl isethionates (SCI), alkyl glyceryl ether sulfonates (AGES), sulfosuccinates, fatty acid soap and the like. These anionic surfactants can be alkoxylated, for example, ethoxylated, although alkoxylation is not required. Examples of classes of anionic surfactants include, but are not limited to, alkyl and alkyl ether sulfates, such as those that may have the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates may be made as condensation products of ethylene oxide and monohydric alcohols having from about 8 to about 24 carbon atoms. In one embodiment, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, or about 3 to about 5, or with about 3, molar proportions of ethylene oxide and the resulting mixture of molecular species having, for example, an average of 3 moles of ethylene oxide per mole of alcohol, is sulfated and neutralized. Examples of anionic surfactants include, but are not limited to, Useful anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, sodium and potassium salts of sodium pareth sulfate, sodium and potassium salts of sodium pareth ether sulfate and combinations thereof.

The fatty acid soap can be any of the neutralized fatty acids, such as those having 8 to 22 carbon atoms. Typical fatty acids used for soaps include, myristic acid, lauric acid, palmitic acid, stearic acids, and other fatty acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils. The fatty acids can be neutralized with any base to form a soap. Typical bases include, but are not limited to, sodium hydroxide, potassium hydroxide, and triethanolamine.

Amphoteric/zwitterionic surfactants may also be included in the composition. These surfactants are typically characterized by a combination of high surfactant activity, lather forming and mildness. Amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines.

Examples of nonionic surfactants include, but are not limited to, sorbitan esters, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof.

Cationic surfactants can also be included in the composition. Examples of cationic surfactants include, but are not limited to any quaternium or polyquaternium compound.

Surfactants can be included in any desired amount. In one embodiment, surfactants are present in the composition in an amount of at least 1% by weight, optionally at least 2, at least 3, at least 4, or at least 5% by weight of the composition. The upper amount can be any typical amount for each type of cleansing composition. A cleansing effective amount is any amount that is typically used for body washes/shower gels, liquid hand soaps, or bar soaps.

When made into an aqueous liquid cleanser, such as a body wash/shower gel or liquid hand soap, surfactants are typically included in amounts up to 40% by weight of the composition. In certain embodiments, the amount is at least 1, 2, 3, 4, 5, 6, 7, 8, 9, or 10 up to 40% by weight of the composition. In certain embodiments, the amount is at least 3% or at least 5% up to 40% by weight of the composition.

When made into a bar soap, surfactants are typically included in amounts of at least 40% by weight of the composition, optionally at least 50, at least 60%, at least 65%, at least 70%, at least 75%, at least 80%, at least 85% by weight of the composition.

In certain embodiments, the cleansing composition contains an anionic surfactant and an amphoteric surfactant, such as sodium laureth sulfate and cocamidopropyl betaine, and optionally a nonionic surfactant, such as cocamide monoethanolamides. Optionally, the cleansing composition can further include a fatty acid soap. These types of cleansing compositions can be in the form of a body wash/shower gel or liquid hand soap.

Other ingredients that can be added to body washes/shower gels, liquid hand soaps, or bar soaps can be included in the cleansing composition. In certain embodiments, body washes/shower gels or liquid hand soaps can contain water in an amount of at least 20% by weight of the composition. In other embodiments, the amount of water is at least 30, at least 40, at least 50, at least 60, at least 70, at least 80, or at least 90% by weight of the composition.

Any of the cleansing compositions can be used in a method to cleanse skin to reduce the attachment of bacteria to skin. After cleansing, the skin can be rinsed with water.

EXAMPLES

The following formula is used for a Liquid Hand Soap composition in the examples.

| Material | Weight % |
|---|---|
| Sodium laureth sulfate | 6.4 |
| Cocamidopropyl betaine | 2.9 |
| Glycerin | 0.7 |
| Sodium Chloride | 0.55 |
| Cocamide monoethanolamide | 0.43 |
| Water and minors (color, fragrance, preservatives) | Q.S. |

Evaluation Procedure for Liquid Hand Soap
Conditioning of Test Skin (VitroSkin™)
1. Cut VitroSkin™ into 2.54 cm square pieces.
2. Add VitroSkin™ to a humidity chamber with 80%/20% water/glycerin.
3. Condition in chamber, room temperature overnight.

Sample Treatment
1. Prepare Soap Slurry by diluting sample as 1:20 (1 part Liquid Hand Soap and 20 parts water=5% LHS in Water) (100 µL LHS with 1900 µL DI Water)
2. Add 2mL of the Soap Slurry into 3 wells of a 6 well polystyrene cell culture plate.
3. Place VitroSkin™, rough side/topography side down, into each well.
4. Place in incubated shaker for 10 min (37° C., speed=80-120 RPM)
5. Remove skin and place in a fresh 6 well plate with 2 mL of DI water. Allow to rinse for 30 secs while shaking the well plate by hand.
6. Remove from rinse water and blot dry.
7. Take reading with chromameter after the VitroSkin™ has been blotted dry, this is the $L_i^*$ and $b_i^*$.
8. Wait 5 minutes then conduct dye solution treatment.

Dye Solution Treatment
9. Add 2 ml of 0.5% Crystal Violet dye solution to 3 wells of a 6 well plate. The dye is prepared 30 minutes or less before use and is kept stirring and protected from light before use.
10. Place a piece of treated VitroSkin™ in each well, rough side/topography side down
11. Soak in dye solution for 2 min at room temperature (25° C.), no shaking, only shake until the piece of skin is immersed in the liquid.
12. Remove VitroSkin™ from dye solution and rinse in 2 mL DI water for 10 sec. Blot dry.
13. Take reading with chroma meter after VitroSkin™ have been blotted dry and allowed to dry (45 min). This is the $L_f^*$ and $b_f^*$.

Data Analysis
14. Measure anti-attachment efficacy based on $\Delta L^*$ ($L_f^*$-$L_i^*$) and $\Delta b(b_f^*-b_i^*)$ value.

Results:
The more negative change in b* indicates a bluer color, or more dye uptake. This corresponds to less coating present on the VitroSkin™.

Using the procedure above, compare results from LHS prototypes with various polymer systems at different levels. When material is added, water is removed. Material weight listed is the as supplied weight added to the LHS along with the active weight of the polymer.

| Material | Wt. % As supplied | Wt. % Active | L* | b* | Delta L* | Delta b* | % Reduction** |
|---|---|---|---|---|---|---|---|
| Polyurethane-34 | 0 | 0 | 68.77 | −39.25 | | | |
| Baycusan ™ C1000 from | 0.5 | 0.2 | 67.98 | −40.42 | −0.79 | −1.17 | 3 |
| Bayer | 1 | 0.4 | 77.74 | −25.86 | 8.96 | 13.39 | −34.1 |
| | 2 | 0.8 | 81.34 | −21.10 | 12.56 | 18.15 | −46.2 |
| | 5 | 2 | 81.94 | −19.66 | 13.17 | 19.60 | −49.9 |

COMPARATIVES

| | Wt. % As supplied | Wt. % Active | L* | b* | Delta L* | Delta b* | % Reduction** |
|---|---|---|---|---|---|---|---|
| Deposilk ™ Q1 | 0 | 0 | 84.61 | −14.79 | | | |
| polyurethane copolymer | 0.5 | 0.325 | 86.93 | −11.47 | 2.32 | 3.32 | −22.5 |
| from Air Products | 1 | 0.65 | 86.9 | −11.54 | 2.29 | 3.25 | −22.0 |
| | 2 | 1.3 | 86.69 | −12.02 | 2.08 | 2.77 | −18.7 |

| | Wt. % As supplied | Wt. % Active | L* | b* | Delta L | Delta b | % Reduction** |
|---|---|---|---|---|---|---|---|
| Polyolprepolymer-2 | 0 | 0 | 79.39 | −22.87 | | | |
| (PPG-12/SMDI | 2 | 2 | 84.71 | −15.18 | 5.32 | 7.69 | −33.6 |
| Copolymer) from Barnet | | | | | | | |

| | Wt. % As supplied | Wt. % Active | L* | b* | Delta L* | Delta b* | % Reduction** |
|---|---|---|---|---|---|---|---|
| Worlee Micromer ™ | 0 | 0 | 79.29 | −23.64 | | | |
| C20/41 ammonium | 0.5 | 0.2 | 82.42 | −17.82 | 4.13 | 5.82 | −24.6 |
| polyacrylate | 1 | 0.4 | 81.31 | −19.35 | 3.02 | 4.28 | −18.1 |
| | 2 | 0.8 | 81.80 | −18.54 | 3.51 | 5.10 | −21.6 |

**% Reduction = 100 * ((test sample b* − 0% control b*)/(0% control b*))

The polyurethane-34 has the most significant improvement versus its 0% polymer placebo (pvalues <0.01 for levels of 1%, 2%, and 5%) compared to the other polyurethane polymers or the acrylate polymer. For the Worlee Micromer and Polyolprepolymer 2, they have p values of less than 0.05.

Evaluation Procedure for Soap Bar
Conditioning of Test Skin (VitroSkin™)
1. Cut VitroSkin™ into 2.54 cm square pieces.
2. Add VitroSkin™ to a humidity chamber with 80%/20% water/glycerin.
3. Condition in chamber, room temperature overnight.

Sample Treatment
1. Prepare soap slurry by diluting sample as 0.5% bar soap in DI Water.
2. Add 10 ml of the soap slurry to a 60 ml jar.
3. Place VitroSkin™, 3 per jar, into the 60 ml jar. (3 are used and the results are averaged)
4. Place in incubated shaker for 60 min (37° C., speed=80-120 RPM).
5. Remove skin and place in a reservoir with 25 ml of DI water. Allow to rinse for 30 seconds, no shaking
6. Remove from rinse water and allow to dry for 45 minutes.

Dye Solution Treatment
7. Add 8 ml of 0.28% Crystal Violet dye each into 6 60 ml jars. The dye is prepared 30 minutes or less before use and is kept stirring and protected from light before use.
8. Place a piece of treated VitroSkin™ in jar (3 in each jar) lightly shake by hand until completely submerged.
9. Soak in dye solution for 5 minutes at room temperature (25° C.), no shaking, only shake until the piece of skin is immersed in the liquid.
10. Remove VitroSkin™ from dye solution and rinse in 25 mL DI water for 30 seconds. Blot dry.
11. Take reading with chroma meter after VitroSkin™ has been blotted dry and allowed to dry (20 min) skin this is the $L_f$ and $b_f$.

Data Analysis
12. Measure anti-attachment efficacy based on the average L*, a*, and b* values after the dye treatment and completely drying.

A soap bar without and a soap bar with 2 weight % (active) polyurethane-34 are tested. The average L*, a*, and b* values of three replicates for each are shown below. The bar soap with polyurethane-34 leaves a residual coating on VitroSkin™ as seen by higher b* values (less blue in color) and higher L* values (more white in color).

| Sample | L* | a* | b* |
|---|---|---|---|
| Bar soap with 2% polyurethane-34 (active weight) | 73.06 | 6.61 | −14.48 |
| Control soap | 65.34 | 14.12 | −27.75 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:
1. A cleansing composition comprising a cleansing effective amount of surfactant and polyurethane-34, wherein the surfactant comprises an anionic surfactant selected from the group consisting of alkyl sulfates, alkyl sulfonates, alkyl phosphates, alkyl ether sulfates, alkyl alpha olefin sulfonates, and fatty acid soap.

2. The cleansing composition of claim 1, wherein the cleansing composition is an aqueous, liquid composition or a bar soap.

3. The cleansing composition of claim 1, wherein the surfactant further comprises an amphoteric surfactant.

4. The cleansing composition of claim 1, wherein the surfactant comprises sodium laureth sulfate and cocamidopropyl betaine.

5. The cleansing composition of claim 1, wherein the cleansing composition is an aqueous liquid composition, and an amount of surfactant is at least 3% by weight of the composition.

6. A cleansing composition comprising a cleansing effective amount of surfactant and polyurethane-34, wherein the cleansing composition is a bar soap, and an amount of surfactant is at least 40% by weight of the composition.

7. The cleansing composition of claim 1, wherein the surfactant is a fatty acid soap.

8. The cleansing composition of claim 1, wherein the amount of polyurethane-34 is 0.1 to 5% by weight of the composition.

9. The cleansing composition of claim 1, wherein the cleansing composition is an aqueous liquid composition containing water in an amount of at least 20% by weight of the composition.

10. A method of reducing attachment of bacteria to skin comprising cleansing skin with a composition of claim 1, and optionally rinsing the skin with water.

* * * * *